United States Patent [19]
White

[11] Patent Number: 5,188,092
[45] Date of Patent: Feb. 23, 1993

[54] DISPOSABLE RIGID ENDOSCOPE

[75] Inventor: Jeffrey S. White, Ridgefield, Conn.

[73] Assignee: United States Surgical Corporation, Norwalk, Conn.

[21] Appl. No.: 626,847

[22] Filed: Dec. 13, 1990

[51] Int. Cl.$^5$ .............................................. A61B 1/00
[52] U.S. Cl. .......................................... 128/4; 128/6; 359/435
[58] Field of Search ............... 128/4, 6; 359/434, 435, 359/785

[56] References Cited

U.S. PATENT DOCUMENTS

| | | |
|---|---|---|
| 2,245,257 | 6/1941 | Crumrine . |
| 2,266,169 | 12/1941 | Crumrine . |
| 2,304,984 | 12/1942 | Wood . |
| 2,341,364 | 2/1944 | Crumrine . |
| 2,388,893 | 11/1945 | Wood . |
| 3,257,902 | 6/1966 | Hopkins . |
| 3,888,568 | 6/1975 | Norris et al. . |
| 4,036,218 | 7/1977 | Yamashita et al. . |
| 4,148,550 | 4/1979 | MacAnally . |
| 4,148,551 | 4/1979 | MacAnally . |
| 4,158,475 | 6/1979 | Dianetti et al. ............ 359/435 |
| 4,354,730 | 10/1982 | Bel ............................. 359/434 |
| 4,385,810 | 5/1983 | Hamou ....................... 359/435 |
| 4,545,652 | 10/1985 | Hoogland . |
| 4,575,195 | 3/1986 | Hoogland . |
| 4,601,710 | 7/1986 | Moll . |
| 4,654,030 | 3/1987 | Moll . |
| 4,664,486 | 5/1987 | Landre et al. . |
| 4,704,007 | 11/1987 | Landre et al. . |
| 4,784,118 | 11/1988 | Fantone et al. . |
| 4,902,280 | 2/1990 | Lander . |
| 4,946,267 | 8/1990 | Hoogland . |
| 4,964,710 | 10/1990 | Leiner . |
| 4,993,817 | 2/1991 | Hoogland ................... 359/435 |
| 5,020,893 | 6/1991 | Kast et al. ................. 359/435 |
| 5,059,009 | 10/1991 | McKinley ................... 359/435 |

OTHER PUBLICATIONS

Pollicove, H. and T. Aquilina, "Injection Mounting: A Lens Assembly Innovation" Photonics Spectra, Dec. 1987, pp. 109–114.

Aquilina, T. D. Richards, H. Pollicove, "Finished Lens Molding", Photonics Spectra, Sep. 1986, pp. 73–80.

Primary Examiner—Gene Mancene
Assistant Examiner—Frank A. LaViola
Attorney, Agent, or Firm—Thomas R. Bremer; Peter G. Dilworth; Rocco S. Barrese

[57] ABSTRACT

A disposable endoscope having an object lens assembly, a relay lens assembly, and an imaging lens assembly with at least the relay lens assembly optical elements being made in whole or in part of molded glass lenses. the relay lens assembly preferably consists of molded glass curved surface lenses arranged in triplet lens configuration with ground or molded glass rod lenses disposed between the curved surface lenses. In preferred embodiments the positive lens elements of each triplet assembly may be bonded in optical contact with the rod lenses or the rod lenses may constitute molded glass lenses incorporating the positive lenses of each triplet. Optical components of the objective and imaging lens assemblies may be of molded or ground glass, and illumination may be conducted by glass or plastic fibers.

26 Claims, 2 Drawing Sheets

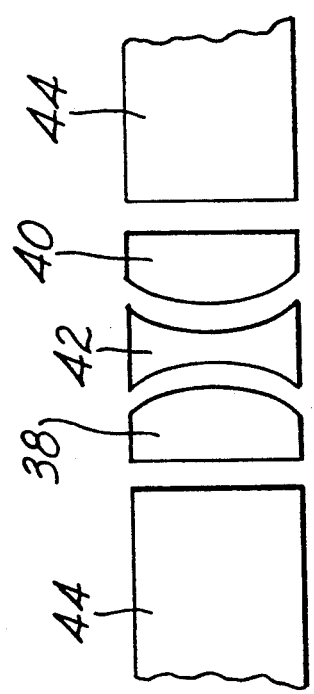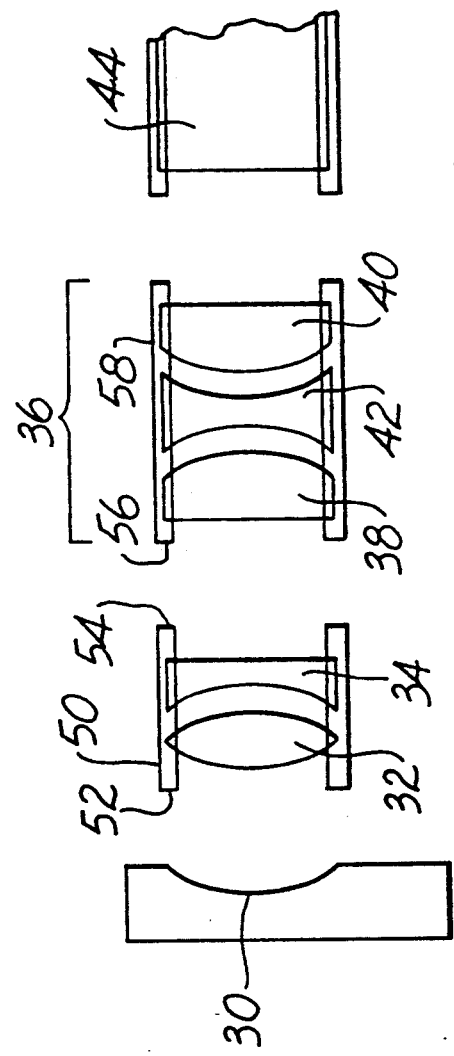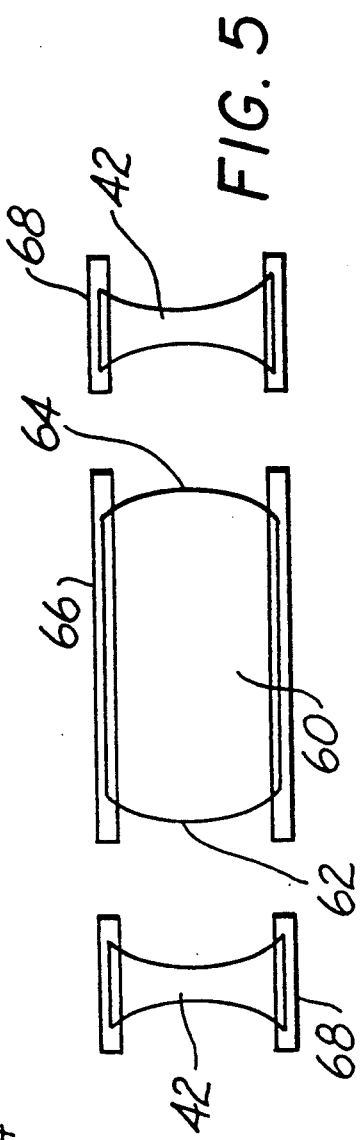

:

DISPOSABLE RIGID ENDOSCOPE

TECHNICAL FIELD

This invention relates to a rigid endoscope and, more particularly, to a disposable rigid endoscope having molded glass optical elements preferably assembled using injection mounting assembly techniques.

BACKGROUND OF THE DISCLOSURE

During surgical procedures it is sometimes necessary to view internal body parts through a small opening which may be on the order of about 10 millimeters in diameter. In particular, it is now common to perform surgical procedures without making a large incision by operating through a plurality of rigid tubes inserted into the body. Procedures of this type, known as endoscopic surgical procedures, provide distinct advantages over traditional surgical procedures in terms of the length and associated cost of the patient's hospital stay and recuperation period. Equally as significant is the substantial reduction in patient discomfort. Instruments for inserting a rigid tube or cannula into the body are disclosed in U.S. Pat. Nos. 4,601,710; 4,654,030 and 4,902,280.

In order to inspect internal parts of the body and/or perform surgery in this fashion, it is necessary for the surgeon to be able to view inside the body without any need for a general opening. The generally accepted method for accomplishing this result is to provide an optical illumination and viewing apparatus known as an endoscope, which is insertable through a cannula. The surgeon may view the image directly through an eyepiece or, more commonly, by projecting the image onto a television screen.

High quality reusable endoscopes have long been known and provide the standard of excellence with respect to image quality. Indeed, the surgical community has come to expect image quality on the order of that provided by reusable endoscopes and will not accept inferior image quality. Unfortunately, however, reusable rigid endoscopes are expensive to purchase and require a high level of maintenance and care and experience degradation in optical image quality with time. Thus, reusable endoscopes must be handled carefully and must be cleaned thoroughly after each use. Cleaning the endoscope requires special training and adds to the cost of the surgical procedure by consuming hospital personnel time.

In order to reduce cost and the potential for transmission of disease or infection there presently is a trend toward use of disposable instruments. Many types of disposable surgical instruments have been provided, but an economical disposable rigid endoscope which provides acceptable image quality has not heretofore been available.

Yamashita U.S. Pat. No. 4,036,218 discloses an endoscope assembled without the use of spacer tubes.

Hoogland U.S. Pat. Nos. 4,545,652 and 4,575,195 disclose flat field lenses for an endoscope wherein Petzval sum correction is dominated by the use of index difference. Hoogland discloses a triplet lens assembly consisting of injection molded polystyrene end elements and a crown glass central element. The indices of refraction and powers of the elements are determined by requiring the Petzval sum to vanish and further requiring a given overall power. The dispersion of the materials are chosen to correct chromatic aberration.

Fantone U.S. Pat. No. 4,784,118 represents one attempt to provide a disposable endoscope, wherein the endoscope light pipe and the objective, relay and viewing lens assemblies all are fabricated of a polymeric material which lends itself to injection molding. Fantone discloses an objective lens system including a plano-concave negative lens and a double convex positive lens to provide a relatively short focal length with a field of view on the order of 60° to 70°. The objective lens system also includes a double convex field lens to reduce or eliminate vignetting at the edge of the field of view. According to Fantone, all concave or convex surfaces of the foregoing lenses preferably are aspheric, and all of the lenses are made, preferably by injection molding, of a polymeric material such as acrylic, polystyrene, polycarbonate or SAN, with acrylic preferred. A relay lens assembly consists of a plurality of injection molded polymeric rod lenses arranged end to end to transmit the image from the objective lens assembly to the proximal end of the endoscope. Fantone's preferred molded polymeric rod lenses are of double convex configuration having entrant and exit refracting surfaces of the same focal length, so that the image from the objective lens assembly is collimated and refocused several times during the relay. A viewing lens system includes a plano concave post rod lens and a strong positive lens, with either a window or a negative lens therebetween. The lens assembly is substantially uncorrected for axial color. Illumination of the body cavity is achieved by disposing a light pipe within a support tube so as to cradle the lens assembly. The light pipe may be fabricated from a molded polymeric material or glass or plastic fibers.

Leiner U.S. Pat. No. 4,964,710 points out several deficiencies in the structure disclosed by Fantone, and proposes a rigid endoscope comprised of a hybrid system incorporating glass plano cylinders with flat polished end faces disposed between molded plastic curved surface lenses having a thickness on the same order of magnitude as their diameter. Leiner further proposes that the plastic lenses can be made of two different types of plastic to allow for the correction of chromatic aberration. Leiner asserts that the plano glass cylinders can be economically made in large quantities, while the plastic lenses can be economically made by known injection molding processes. Like Fantone, Leiner discloses objective, relay and ocular lens assemblies. The objective lens system includes a field widening lens, a prism and objective lenses. These elements may be made of molded plastic, as taught by Fantone, or they may be made of conventional ground glass. The Leiner relay lens system comprises an even number of molded polymeric curved surface lenses. Leiner shows each plastic lens assembly as a lens pair and states that the lenses of each pair may be made of two different types of plastic material.

Notwithstanding the disclosures of Fantone and Leiner, there remains a need for an economical disposable endoscope which attains high quality imaging. Fantone and Leiner each make use of molded plastic optical components in an attempt to reduce cost, but the number of appropriate plastic materials is few, which limits the freedom of the optical designer to select from a variety of materials to reduce or eliminate chromatic aberration. Furthermore, the optical design disclosed by Fantone tends to focus any manufacturing defects or flaws at the image surface, and the paired lens configuration proposed by Leiner is not conducive to achieving reduced field curvature.

Therefore, a relatively low cost disposable endoscope is needed which provides the optical designer with greater degrees of freedom in selecting lens materials to correct for chromatic and other aberrations and which incorporates improved optical design so as to eliminate real or potential imaging problems of Fantone and/or Leiner.

SUMMARY OF THE INVENTION

In accordance with the invention an endoscope is provided which includes an objective lens assembly, a relay lens assembly, and an imaging lens assembly. Illumination is conveyed to the distal end of the endoscope to illuminate the scene to be viewed. Reflected illumination from the field enters the endoscope through the objective lens assembly and is conveyed by the relay lens assembly to the imaging lens assembly, which focuses the image for direct viewing or detection and display on a television screen.

The relay lens assembly consists of a series of glass rod lenses and molded glass curved surface lenses. Preferably, the curved surface lenses are arranged in a triplet configuration of positive, negative and positive lenses, respectively, disposed between rod lenses. In alternative embodiments the positive lens elements are bonded to adjacent rod lenses or are formed integrally therewith. In a still further embodiment, the positive lens elements and rod lenses are integrally formed by molded glass technology. The preferred triplet configuration provides reduced chromatic aberration and field curvature.

Optical elements of the object and imaging lens assemblies may be of ground or molded glass, and may be configured and arranged in accordance with known principles.

In alternative embodiments one or more lens assemblies are constructed in accordance with injection mounting techniques. That is, one or more of the objective, relay and/or image lens assemblies may be constructed in whole or in part as subassemblies of one or more molded glass lens elements which are mounted by injection mounting. In particular, curved surface lens subassemblies may be mounted by injection mounting with each subassembly including alignment surfaces to facilitate positioning of curved surface lenses relative to adjacent rod assemblies or, if appropriate, the object or imaging lens assemblies. Advantageously, subassemblies constructed in this manner may quickly be assembled to provide proper spacing of optical elements without any need for further alignment, obviating the need for alignment fixtures and personnel skilled in the art of aligning optical elements. Thus, it is contemplated that injection mounted subassemblies may readily be disposed and aligned within an outer tubular housing of the endoscope to reduce manufacturing costs and provide consistent results.

BRIEF DESCRIPTION OF THE DRAWINGS

FIG. 3 is an enlarged partial elevation view in exaggerated detail of a first alternative embodiment of the invention;

FIG. 4 is an enlarged partial cross-section view in exaggerated detail of an endoscope optical system constructed of subassemblies made in accordance with injection mounting assembly techniques; and FIG. 5 is an enlarged partial cross-section view in exaggerated detail of alternative endoscope subassemblies constructed in accordance with the invention.

DETAILED DESCRIPTION OF THE PREFERRED EMBODIMENTS

Figure 1:
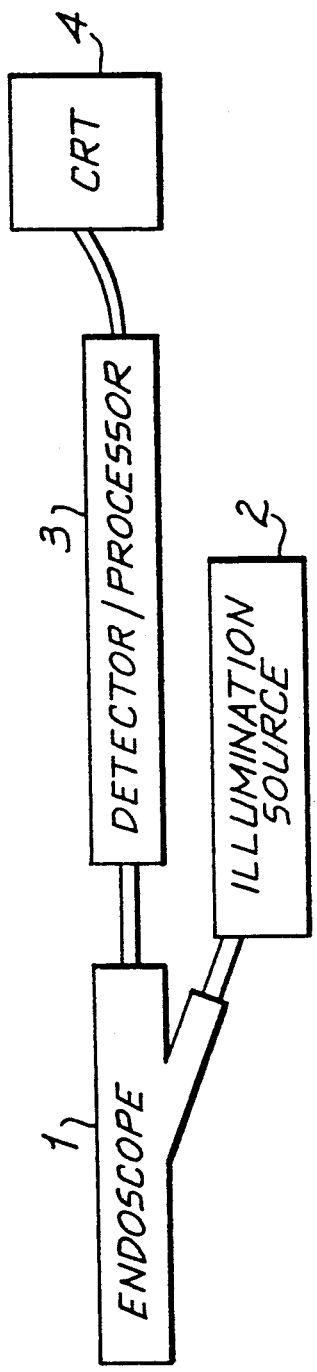
FIG. 1 is a block diagram illustration of an endoscope system.

Referring now to the accompanying drawings, particularly FIG. 1, an endoscope system generally includes an endoscope 1, an illumination source 2, a detector/processor 3 and a cathode ray tube (CRT) 4, i.e. a television screen.

Figure 2:
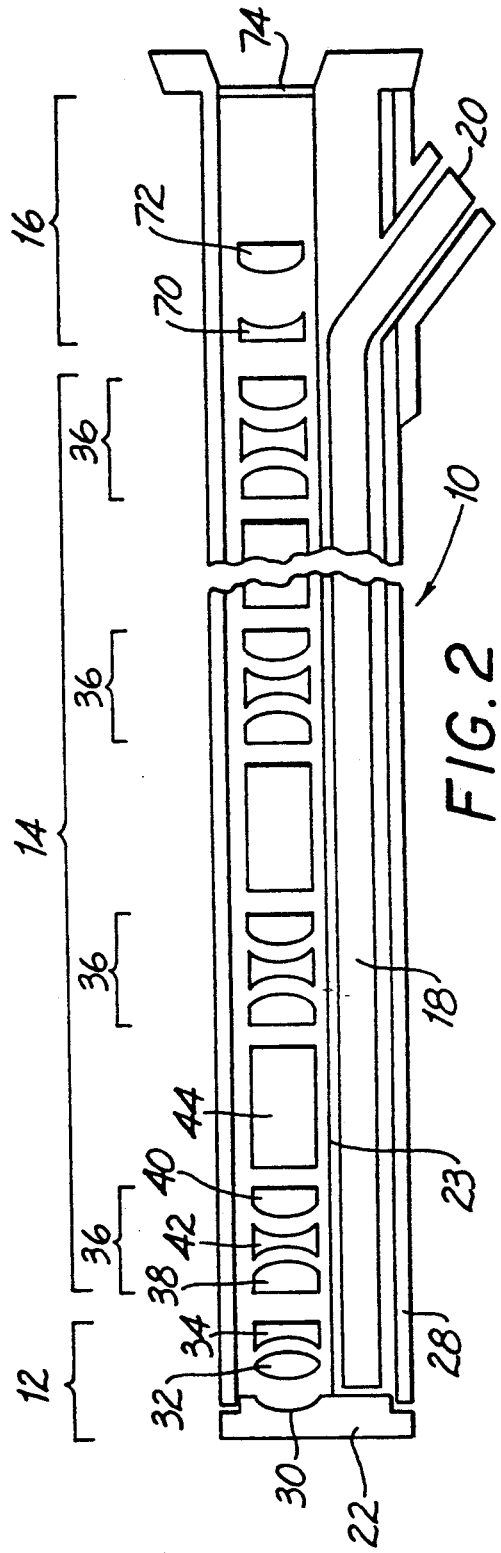
FIG. 2 is an enlarged cross-section view in exaggerated detail of an endoscope constructed in accordance with the invention.

FIG. 2, a cross-sectional view of an endoscope constructed in accordance with the invention, illustrates an endoscope 10 having a distal objective lens assembly 12, an intermediate relay lens assembly 14, and a proximal imaging lens assembly 16. An illumination transmission member 18 is also provided for conveying illumination from a proximal illumination coupling port 20 to the distal tip of the endoscope. Proximal illumination source 2 (see FIG. 1) is connected to illumination coupling port 20 to transmit light into transmission member 18, which conveys the light to the distal tip of the endoscope to illuminate the field beyond the endoscope tip. Reflected light from the field is collected by the objective lens assembly 12, transmitted through the relay lens assembly, and focussed by imaging lens assembly 16. The focussed image may be viewed directly or, in most instances, will be detected by a detector/processor apparatus 3 (see FIG. 1) which detects and processes the image to create a television display on cathode ray tube 4. A generally cylindrical endoscope housing 28 encloses and supports the illumination transmission element and lens assemblies. The housing defines a distal tip and a proximal viewing port configured to be coupled to a viewing eyepiece (not shown) or a detector/processor. A baffle or light shield 23 may be provided to reduce spurious light which might otherwise detract from the image.

Referring again to FIG. 2, objective lens assembly 12 includes a field lens 30 and at least one objective lens element, shown for convenience as a doublet (cemented or uncemented) comprised of lens elements 32 and 34. As shown, field lens 30 preferably is formed integrally with the distal window 22 of the endoscope, and light transmission member 18 projects light through the window adjacent the field flattening lens.

Relay lens assembly 14 consists of a plurality of curved surface relay lens elements 36 with rod lenses disposed therebetween. Preferably, each curved surface relay lens assembly 36 constitutes a lens triplet (cemented or uncemented) having two positive lens elements 38, 40 with a negative lens element 42 therebetween. This configuration advantageously permits both the reduction of chromatic aberrations and substantial elimination of field curvature to provide a flat field. That is, the Petzval sum of the lens triplet can be made to approximate zero while, at the same time, a positive lens power is achieved. As shown in FIG. 2, rod lenses 44 may be plano-plano glass cylinders. Alternatively, curved surfaces may be provided on the rod lenses, if desired. Preferably all exposed lens surfaces are coated with anti-reflection coatings, and curved lens surfaces should be aspheric to reduce or eliminate spherical aberrations.

In a first alternative embodiment shown in FIG. 3, positive lens elements 38, 40 are bonded to adjacent rod lenses using an appropriate optical cement, such as an ultraviolet radiation curing optical cement. This construction advantageously reduces the number of exposed lens surfaces which must be coated.

In accordance with the invention all lens elements are constructed of glass in order to provide maximum freedom of choice of materials so that optimum color correction, index selection and field flattening can be achieved without the potential for imaging problems created by prior plastic lenses disclosed by Fantone and Leiner.

Also in accordance with the invention, most if not all lens elements are made using molded glass technology. Use of molded glass lenses significantly reduces the manufacturing cost of the endoscope, making it possible to provide a disposable endoscope having high quality glass lenses which provide the best image possible. Thus, individual lenses described above may be made by molded glass technology. In an alternative embodiment, a construction similar to that illustrated in FIG. 3 could be achieved by molding lenses 38, 40 integral with rod lenses 44 (see FIG. 5, discussed below).

To further reduce the cost and optimize image quality of the endoscope, molded glass lens elements preferably are mounted using injection mounting assembly techniques. Referring now to FIG. 4, by way of example, objective lens elements 32, 34 may be mounted by injection mounting as a first subassembly 50 having a front surface 52 configured to abut the endoscope window 22 adjacent to the field flattening lens. The injection mounting assembly housed in endoscope tube 28 defines a predetermined position of the objective lens elements relative to field flattening lens 30. The objective subassembly also includes a rear positioning surface 54 for determining the positional spacing of subsequent lens elements or subassemblies. As shown in FIG. 4, curved surface relay lens assemblies 36 consist of lens elements 38, 40, 42 mounted by injection mounting to form a subassembly 58. The front positioning surface 56 of the first curved surface relay lens subassembly 58 engages the rear positioning surface 54 of the objective subassembly 50 to dispose all lens elements in predetermined alignment. Thereafter, a series of rod lenses 40, which also may be injection mounted to form a rod lens subassembly 59, and curved surface relay lens subassemblies are positioned in alternating relation in order to readily assemble the lens elements with proper positional spacing and alignment. It is contemplated that predetermined positioning of field lens 30 and all optical subassemblies in housing 28 will readily position and space all optical elements without any need for more complex alignment and positioning structures and assemblies. As will readily be appreciated, a wide variety of subassembly configurations may facilitate assembly of the endoscope. By way of example only, the rod lenses could be commonly mounted in the same subassembly as the curved surface relay lenses using injection mounting techniques or the entire optical system could be injection mounted as a single subassembly.

By way of further example, FIG. 5 illustrates an integral molded combination rod lens and positive lens element 60 having curved end surfaces 62, 64. Integral molded lens element 60 is injection mounted as a rod lens subassembly 66. As shown, in this configuration molded glass negative lens 42 preferably is injection mounted to create a negative lens subassembly 68. Subassemblies 66, 68 may be easily assembled in alternating abutting relation so as to create a relay lens assembly with negative lenses 42 properly aligned and spaced relative to positive rod lens elements 60.

Of course, individual lens elements could be mounted using traditional spacer tubes, but such a construction requires greater skill to assemble and align the lens elements, contributing to the cost of presently available reusable endoscopes. The use of both molded glass lens technology and injection mounting makes it possible to quickly assemble endoscopes without highly trained labor in such a manner that all lens elements are quickly and accurately positioned and aligned.

Imaging lens assembly 16 also may be made of molded glass lenses mounted using injection mounting techniques. The imaging lens generally consists of one or more lenses 70, 72 configured and arranged to focus the image beyond the proximal end window 74 of the endoscope, preferably on a detector which forms part of a detector/processor 3 for processing the image for display on a television CRT 4. The distal endoscope window and field lens may be of ground or molded glass. The endoscope optical system also should have a hyperfocal distance suitable to maintain the entire operative field in focus at all times.

Those of ordinary skill in the art will readily appreciate that an endoscope constructed in accordance with the invention provides an endoscope having all the optical design and performance advantages of a traditional reusable endoscope. However, use of molded glass lens technology and injection mounting assembly substantially reduces the cost of the endoscope so that, for the first time, a high quality disposable endoscope may be provided.

While the foregoing specification contains many specifics, those of ordinary skill in the art will appreciate that numerous variations and modifications may be made while remaining within the scope of the appended claims.

What is claimed is:

1. An endoscope comprising:
   objective lens means;
   a relay lens system proximal of said objective lens means comprised of at least two molded glass curved surface triplet lens assemblies separated by at least one rod lens, each said triplet lens assemblies including first and second positive curved surface thin lenses separated by a negative curved surface thin lens; and
   imaging lens means proximal of said relay lens system, said objective lens means, relay lens system and imaging lens means axially aligned to convey an image from a field through said objective lens means, relay lens system and imaging lens means.

2. The endoscope of claim 1 wherein said molded glass curved surface lenses of said triplet lens assemblies are injection mounted to form curved surface lens subassembies.

3. The endoscope of claim 2 wherein said curved surface lens subassemblies each include at least one positioning surface.

4. The endoscope of claim 3 wherein said relay lens system comprises a series of curved surface lens subassemblies with rod lenses therebetween, said at least one positioning surface determining the position of each curved surface lens relative to adjacent rod lens.

5. The endoscope of claim 1 wherein said relay lens system comprises a series of said triplet lens assemblies and said rod lenses mounted by injection mounting.

6. The endoscope of claim 1 wherein said objective lens means comprises at least one molded glass optical element mounted by injection mounting.

7. The endoscope of claim 1 wherein said imaging lens means comprises at least one molded glass optical element mounted by injection mounting.

8. The endoscope of claim 1 wherein said objective lens means comprises a field lens and at least one objective lens.

9. The endoscope of claim 8 wherein said field lens and said objective lens are made of ground glass.

10. The endoscope of claim 8 wherein said field lens and said objective lens are made of molded glass.

11. The endoscope of claim 1 further comprising illumination means for illuminating a field distal to said object lens means.

12. The endoscope of claim 1 wherein said image is displayed electronically on a cathode ray tube.

13. The endoscope of claim 1 wherein said imaging lens means comprise means for focusing said image.

14. The endoscope of claim 1 wherein said triplet assembly has approximately zero Petzval sum.

15. The endoscope of claim 1 wherein at least one of said positive lenses is bonded to a rod lens.

16. The endoscope of claim 1 wherein said triplet lens assembly is at least partially integrated into adjacent rod lenses.

17. The endoscope of claim 16 wherein said first positive lens is integral with a first rod lens and said second positive lens is integral with a second rod lens.

18. The endoscope of claim 17 wherein each said rod lens and integral positive lens is of molded glass construction.

19. An endoscope imaging system comprising:
an illumination source;
an endoscope comprising:
  means for transmitting illumination from said illumination source to a distal field;
  distal objective lens means;
  a relay lens system proximal of said objective lens means including at least two molded glass curved surface triplet lens assemblies separated by at least one rod lens, each said triplet lens assemblies including first and second positive curved thin lenses separated by a negative curved surface thin lens; and
  imaging lens means proximal of said relay lens system for focusing an image of the illuminated field, said image transmitted to said imaging lens means by said objective lens means and said relay lens system;
means for detecting said focussed image; and
means for displaying said detected image.

20. The endoscope imaging system of claim 19 wherein said objective lens means, said at least one rod lens and said imaging lens means comprise a plurality of molded glass lenses.

21. The endoscope imaging system of claim 19 wherein said objective lens means, said relay lens system and said imaging lens means are injection mounted.

22. A method of making an endoscope comprising:
providing illumination means for illuminating a distal field;
providing distal objective lens means for receiving an image from the illuminated distal field;
providing at least two molded glass curved surface triplet lens assemblies separated by at least one rod lens to provide an intermediate relay lens assembly for proximally transmitting an image received from said distal objective lens means, each said triplet lens assemblies including first and second positive curved surface thin lenses separated by a negative curved surface thin lens; and
providing imaging lens means proximal of said intermediate relay lens assembly for receiving an image from said intermediate relay lens assembly and focusing the image for viewing.

23. The method of claim 22 wherein said step of providing an intermediate relay lens assembly further comprises providing at least two molded glass curved surface lenses mounted by injection mounting separated by at least one rod lens.

24. The method of claim 22 wherein said step of providing an intermediate relay lens assembly further comprises providing at least one molded glass rod lens integrally molded with at least one curved surface positive lens element and at least one negative lens element spaced therefrom.

25. The method of claim 24 wherein said integrally molded rod lens and positive lens element are injection mounted.

26. The method of claim 24 wherein said negative lens element is made of molded glass and is injection mounted.

* * * * *